United States Patent
Nakanishi et al.

(10) Patent No.: US 8,731,265 B2
(45) Date of Patent: May 20, 2014

(54) X-RAY COMPUTED TOMOGRAPHY APPARATUS, MEDICAL IMAGE PROCESSING APPARATUS, X-RAY COMPUTED TOMOGRAPHY METHOD, AND MEDICAL IMAGE PROCESSING METHOD

(75) Inventors: Satoru Nakanishi, Utsunomiya (JP); Satoshi Saito, Yaita (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 816 days.

(21) Appl. No.: 12/631,338

(22) Filed: Dec. 4, 2009

(65) Prior Publication Data

US 2010/0150421 A1    Jun. 17, 2010

(30) Foreign Application Priority Data

Dec. 11, 2008 (JP) ................ 2008-315995
Nov. 27, 2009 (JP) ................ 2009-269729

(51) Int. Cl.
*A61B 6/03* (2006.01)
*G06T 11/00* (2006.01)
*G01N 23/04* (2006.01)
*A61B 6/00* (2006.01)

(52) U.S. Cl.
CPC ............. *G06T 11/006* (2013.01); *A61B 6/032* (2013.01); *G01N 23/046* (2013.01); *A61B 6/4085* (2013.01); *Y10S 378/901* (2013.01)
USPC ............................... 382/131; 378/4; 378/901

(58) Field of Classification Search
CPC .... A61B 6/032; A61B 6/4085; G06T 11/006; G01N 23/046
USPC ................. 378/4, 19, 901; 382/131
See application file for complete search history.

(56) References Cited

U.S. PATENT DOCUMENTS

| | | | | |
|---|---|---|---|---|
| 5,708,691 | A * | 1/1998 | Zmora | 378/4 |
| 5,825,842 | A | 10/1998 | Taguchi | |
| 5,838,756 | A * | 11/1998 | Taguchi et al. | 378/4 |
| 6,118,841 | A * | 9/2000 | Lai | 378/19 |
| 6,269,141 | B1 | 7/2001 | Proksa et al. | |
| 6,922,457 | B2 * | 7/2005 | Nagata et al. | 378/19 |

(Continued)

FOREIGN PATENT DOCUMENTS

| | | |
|---|---|---|
| JP | 9-19425 A | 1/1997 |
| WO | 99/01067 | 1/1999 |

OTHER PUBLICATIONS

European Patent Office Extended Search Report dated Mar. 12, 2010 for related EP Application No. 09015316.4.

(Continued)

*Primary Examiner* — Allen C. Ho
(74) *Attorney, Agent, or Firm* — Yoshida & Associates, LLC

(57) ABSTRACT

An X-ray computed tomography apparatus includes, an X-ray source which irradiates an object with X-rays spreading in a slice direction, an X-ray detector including a plurality of X-ray detection elements which are juxtaposed in the slice direction and detect X-rays transmitted through the object, a reconstruction unit which includes a back-projection unit which obtains back-projection data relating to each of a plurality of pixels defined in an imaging area by performing back projection of data acquired by the X-ray detector and an interpolation unit which interpolates the data, and performs reconstruction processing for an image, and a setting unit which sets central positions of a plurality of pixels in the imaging area in the reconstruction processing to positions offset from positions corresponding to centers of the X-ray detection elements in the slice direction.

14 Claims, 10 Drawing Sheets

(56) References Cited

U.S. PATENT DOCUMENTS 7,251,306 B2 * 7/2007 Sauer et al. .................. 378/4
7,583,780 B2 * 9/2009 Hsieh et al. .................. 378/4

OTHER PUBLICATIONS

Noo et al, "General Reconstruction Theory for Multislice X-ray Computed Tomography With a Gantry Tilt", Sep. 2004, pp. 1109-1116, IEEE Transactions on Medical Imaging, vol. 23, No. 9.
EP Office Action dated Aug. 25, 2011 for corresponding EP Application No. 09015316.4.
Galigekere, Ramesh R, "Cone-Beam Reprojection Using Projection-Matrices", IEEE Transactions on Medical Imaging, vol. 22, No. 10, Oct. 2003, pp. 1202-1214.

* cited by examiner

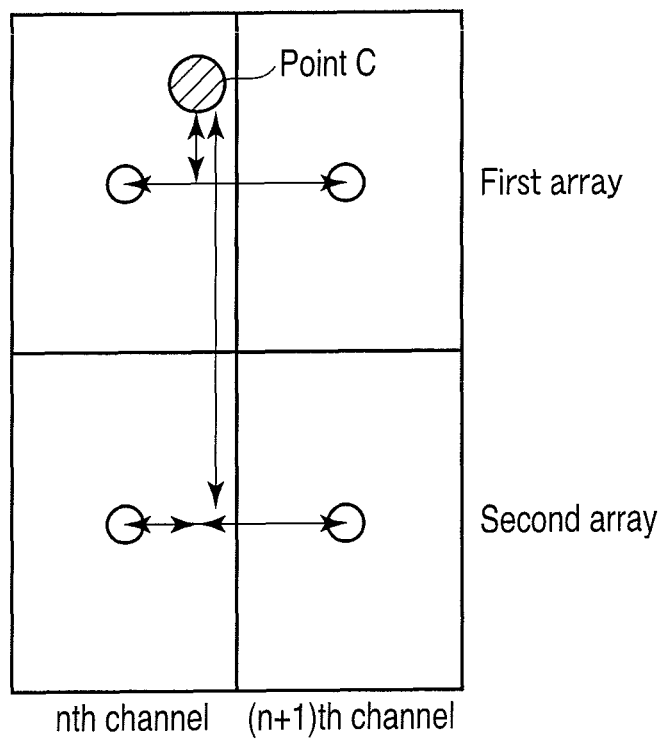
F I G. 8

(2) $z = \frac{SW}{4} + \frac{SW}{2} \cdot n \ (n=\pm 0, \pm 1, \pm 2, \cdots)$ Case in which (0.25-mm intervals)

(3) $z = \frac{SW}{4} + SW \cdot n \ (n=\pm 0, \pm 1, \pm 2, \cdots)$ Case in which (0.5-mm intervals)

(1) $z = \frac{SW}{2} + SW \cdot n \ (n=\pm 0, \pm 1, \pm 2, \cdots)$ Case in which (0.5-mm intervals)

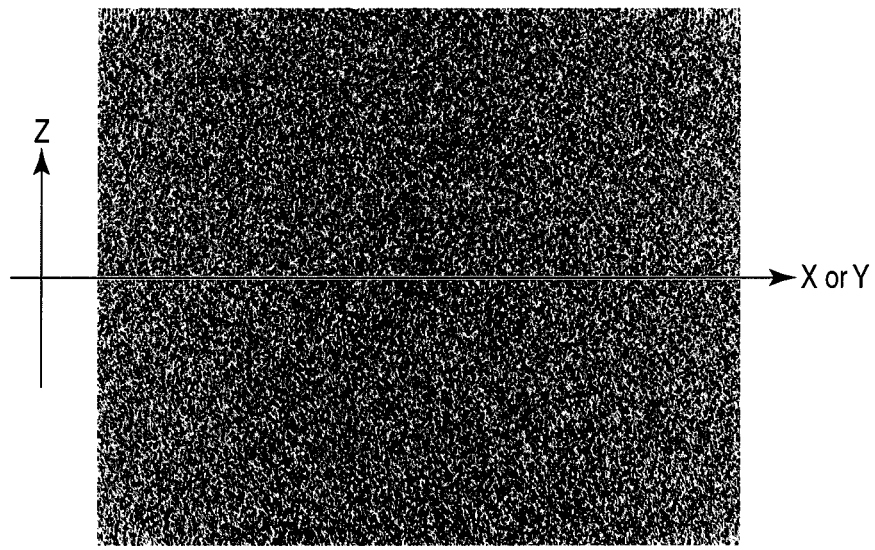
F I G. 10
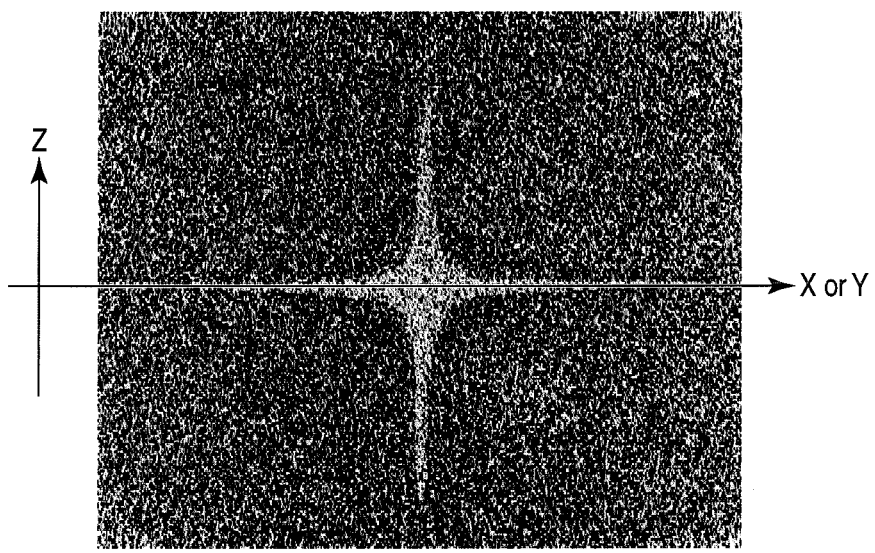
F I G. 12

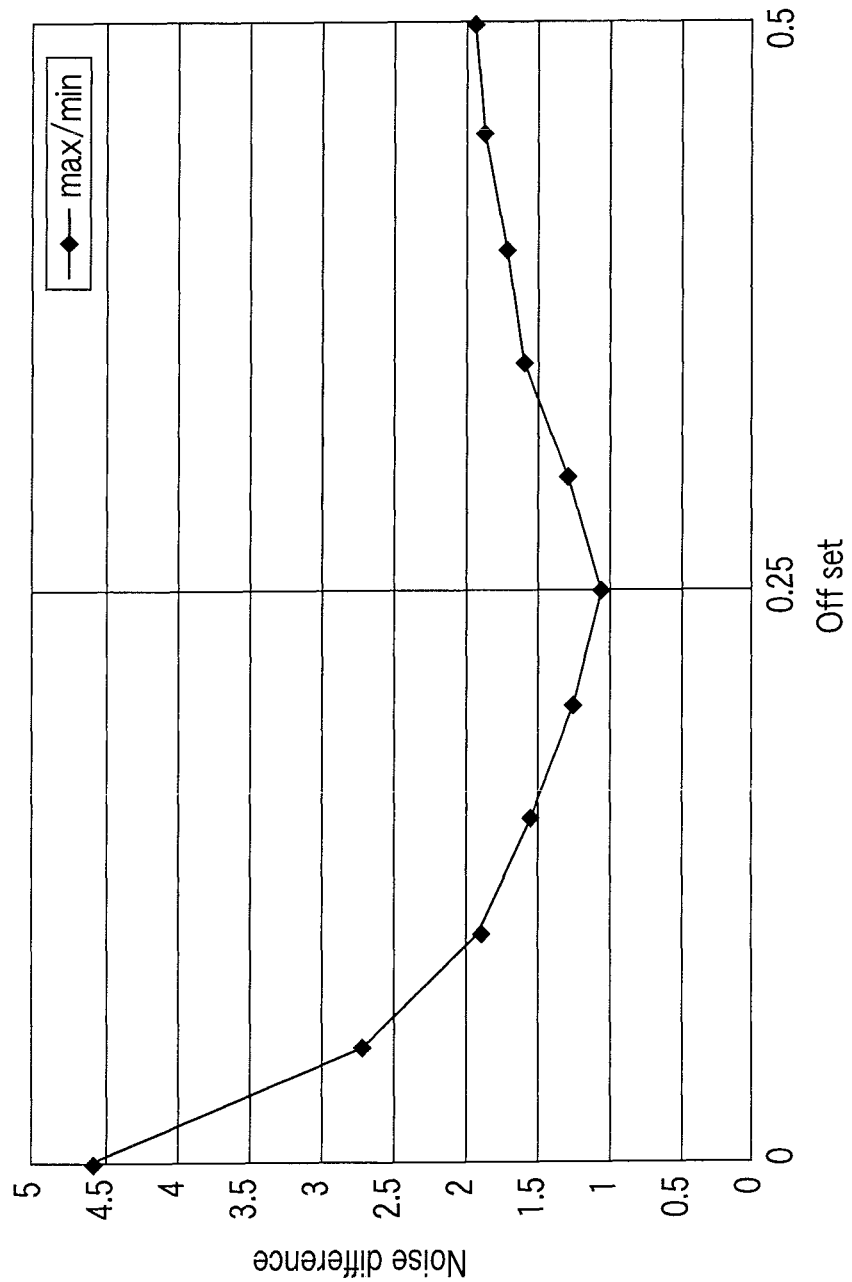
F I G. 13

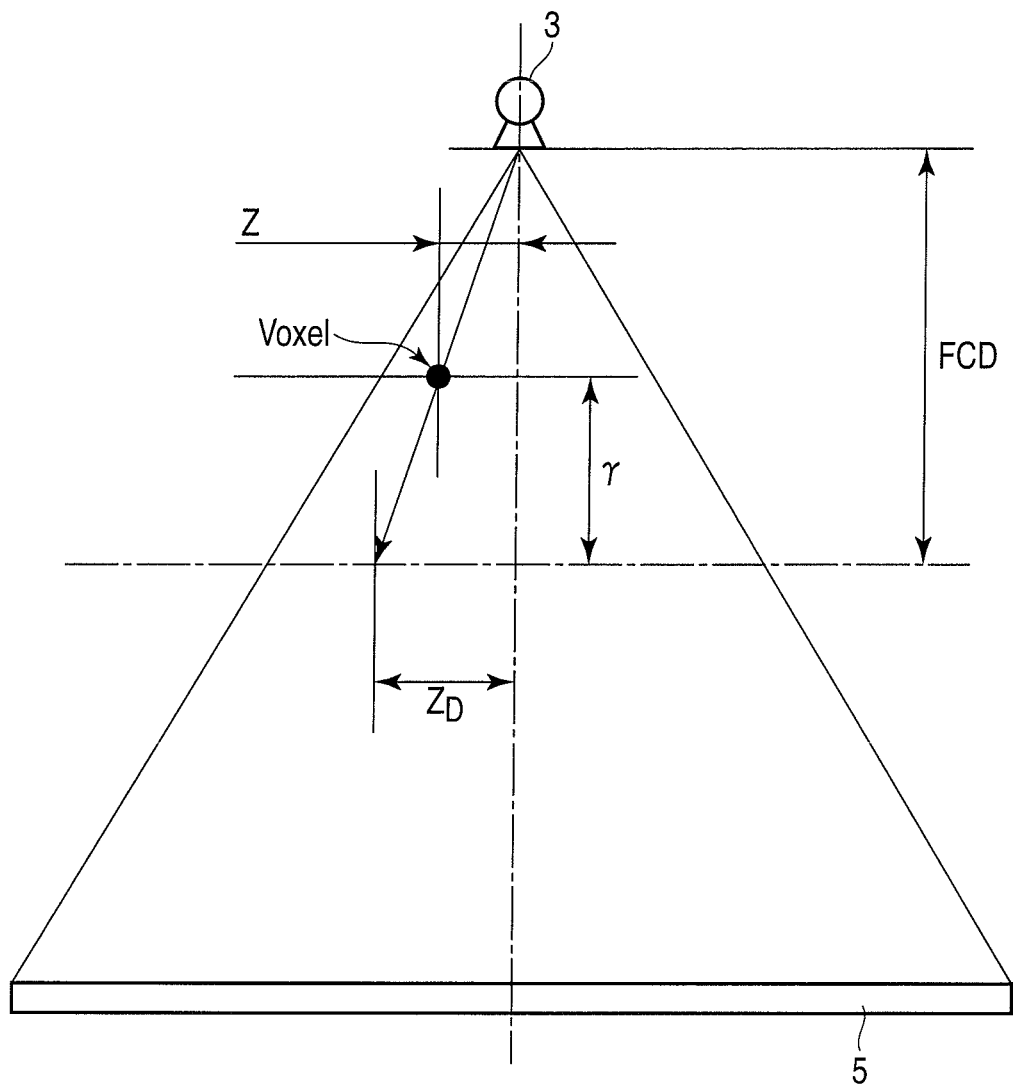
F I G. 14

X-RAY COMPUTED TOMOGRAPHY APPARATUS, MEDICAL IMAGE PROCESSING APPARATUS, X-RAY COMPUTED TOMOGRAPHY METHOD, AND MEDICAL IMAGE PROCESSING METHOD

CROSS-REFERENCE TO RELATED APPLICATIONS

This application is based upon and claims the benefit of priority from prior Japanese Patent Applications No. 2008-315995, filed Dec. 11, 2008; and No. 2009-269729, filed Nov. 27, 2009, the entire contents of both of which are incorporated herein by reference.

BACKGROUND OF THE INVENTION

1. Field of the Invention

The present invention relates to an X-ray computed tomography apparatus, medical image processing apparatus, X-ray computed tomography method, and medical image processing method which scan objects with X-rays.

2. Description of the Related Art

Among X-ray computed tomography apparatuses like that disclosed in, for example, Jpn. Pat. Appln. KOKAI Publication No. 9-19425, a third-generation scanning system is known, which includes an X-ray tube including an X-ray source to produce an X-ray fan beam and a one-dimensional array X-ray detector to acquire projection data from various angles while rotating around an object.

There are available, for example, a conventional scanning system in which an X-ray tube revolves on the same circular orbit and a helical scanning system defined as a scanning system in which an X-ray source and a one-dimensional array X-ray detector continuously rotate around an object, and a bed on which the object is placed moves along the body axis in synchronism with the rotation.

In addition, a conic beam scanning system (also called a multi-slice scanning system) is known, in which an X-ray source to produce an X-ray conic beam in a conical shape is combined with a two-dimensional array detector having a plurality of one-dimensional array detectors stacked in N arrays in the Z-axial direction, and projection data is acquired while the X-ray source and the detector keep facing each other and rotate around an object.

Considering an X-ray beam striking a given detector array, a basic slice thickness in the conic beam scanning system is defined as a thickness in the Z-axial direction when the X-ray beam passes through the rotation center (Z-axis), and an imaging area FOV in the conic beam scanning system is defined as a cylinder having a radius co centered on the Z-axis.

As a reconstruction processing method to be used when a conic beam scanning system is implemented by a conventional scanning system, the Feldkamp (FDK) reconstruction method is known.

This FDK reconstruction method is an approximate three-dimensional reconstruction algorithm obtained by extending a fan beam (within a two-dimensional plane) reconstruction algorithm, which is a mathematically strict reconstruction method, in the Z-axial direction. This algorithm includes the following steps 1, 2, and 3: (1) multiplying the weighted projection data of projection data by a value dependent on a Z-coordinate; (2) performing convolution computation between the data obtained in step 1 and the same reconstruction function as the fan beam data (convolution computation); and (3) performing back projection of the data obtained in step 2 onto a path through which the X-rays have passed (from the focus to each channel of the detector). Back-projection processing is performed through 360°.

In these reconstruction methods, the central position of each voxel in the imaging area FOV is generally set in correspondence with the central position of a corresponding X-ray detection element of the X-ray detector. That is, the center of each voxel is defined on a line connecting a corresponding X-ray detection element and the X-ray focus. In this case, an X-ray beam has a conic beam shape spreading in the slice direction. Owing to this spread, the degree of interpolation varies depending on the position of each detection element in the slice direction.

The above techniques, however, have the following problem. That is, interpolation becomes uneven depending on the positions of detection elements in the slice direction. For example, almost no interpolation is performed at the central position. This degrades an image SD near the axis of rotation, which is the central position, and the mid-plane, which is a central cross-section in the array direction of the detector. When this is expressed in MIP, a cross-shaped artifact occurs at the central position, as shown in FIG. 12.

BRIEF SUMMARY OF THE INVENTION

An example of the present invention is an X-ray computed tomography apparatus comprising, an X-ray source which irradiates an object with X-rays spreading in a slice direction; an X-ray detector comprising a plurality of X-ray detection elements which are juxtaposed in the slice direction and detect X-rays transmitted through the object, a reconstruction unit which comprises a back-projection unit which obtains back-projection data relating to each of a plurality of pixels defined in an imaging area by performing back projection of data acquired by the X-ray detector and an interpolation unit which interpolates the data, and performs reconstruction processing for an image, and a setting unit which sets central positions of a plurality of pixels in the imaging area in the reconstruction processing to positions offset from positions corresponding to centers of the X-ray detection elements in the slice direction.

An another example of the present invention is a medical image processing apparatus comprising, a storage unit which stores data acquired by an X-ray CT apparatus, a reconstruction unit which comprises a back-projection unit which obtains back-projection data relating to each of a plurality of pixels defined in an imaging area by performing back projection of the acquired data and an interpolation unit which interpolates the data, and performs reconstruction processing for an image; and a setting unit which sets central positions of a plurality of pixels in the imaging area in the reconstruction processing to positions offset from positions corresponding to centers of the X-ray detection elements of the X-ray CT apparatus in the slice direction.

An another example of the present invention is an X-ray computed tomography method using an X-ray computed tomography apparatus, the method comprising, irradiating an object with X-rays spreading in a slice direction, detecting X-rays transmitted through the object by using an X-ray detector comprising a plurality of X-ray detection elements which are juxtaposed in the slice direction, performing reconstruction processing for an image comprising obtaining back-projection data relating to each of a plurality of pixels defined in an imaging area by performing back projection of the data acquired in detecting and interpolating the data, and setting central positions of a plurality of pixels in the imaging area in the reconstruction processing to positions offset from positions corresponding to centers of the X-ray detection elements in the slice direction.

An another example of the present invention is a medical image processing method using a medical image processing apparatus, the method comprising, storing data acquired by an X-ray CT apparatus, performing reconstruction processing for an image comprising obtaining back-projection data relating to each of a plurality of pixels defined in an imaging area by performing back projection of the acquired data and interpolating the data, and setting central positions of a plurality of pixels in the imaging area in the reconstruction processing to positions offset from positions corresponding to centers of the X-ray detection elements in the slice direction.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8 is a view showing the relationship between an X-ray beam and a reconstruction voxel in the reconstruction processing when viewed from a direction perpendicular to the X direction;

FIG. 10 is a view showing an MIP image of reconstructed volume data obtained by reconstruction processing according to the first embodiment;

FIG. 12 is a view showing an MIP image of an example of reconstructed volume data;

FIG. 13 is a graph showing the relationship between the offsets and noise differences of reconstructed volume data; and FIG. 14 is a view for explaining the back-projection processing according to the first embodiment of the present invention.

DETAILED DESCRIPTION OF THE INVENTION

An embodiment of the present invention will be described below with reference to the views of the accompanying drawing.

First Embodiment

Figure 1:
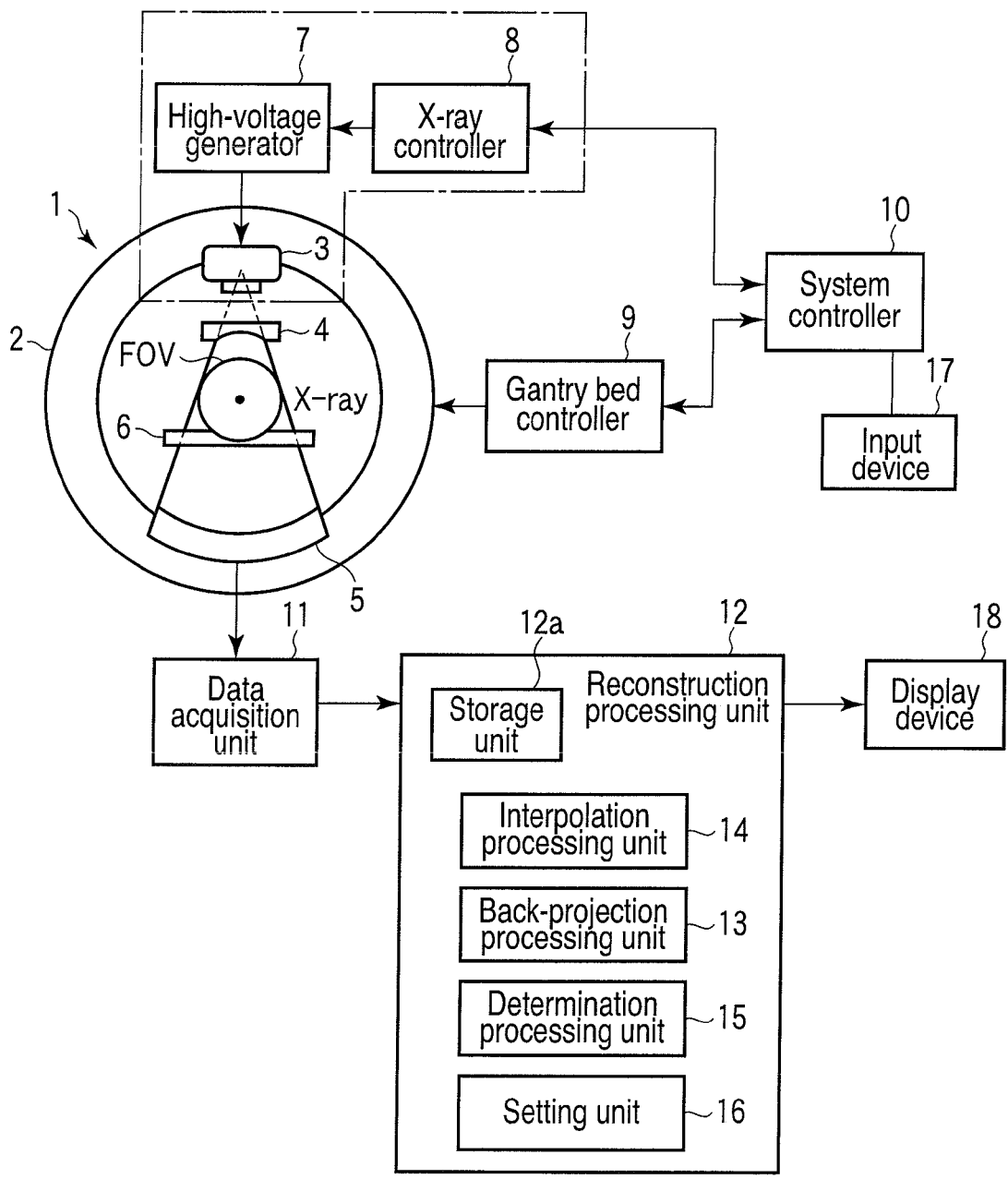
FIG. 1 is a block diagram showing the arrangement of an X-ray computed tomography apparatus according to the first embodiment of the present invention.
Figure 2:
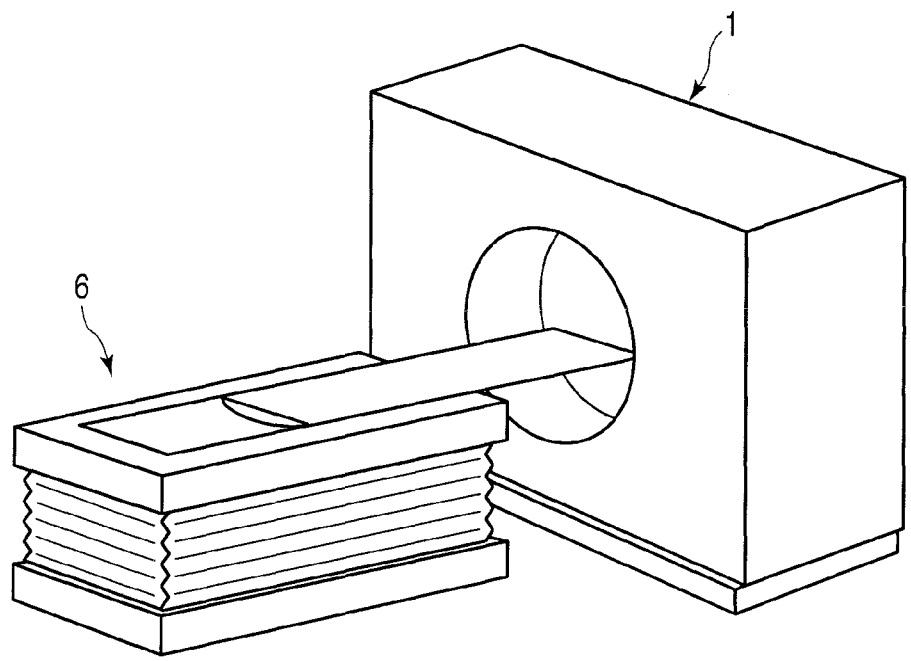
FIG. 2 is a perspective view showing the outer appearance of the gantry of the X-ray computed tomography apparatus.
Figure 3:
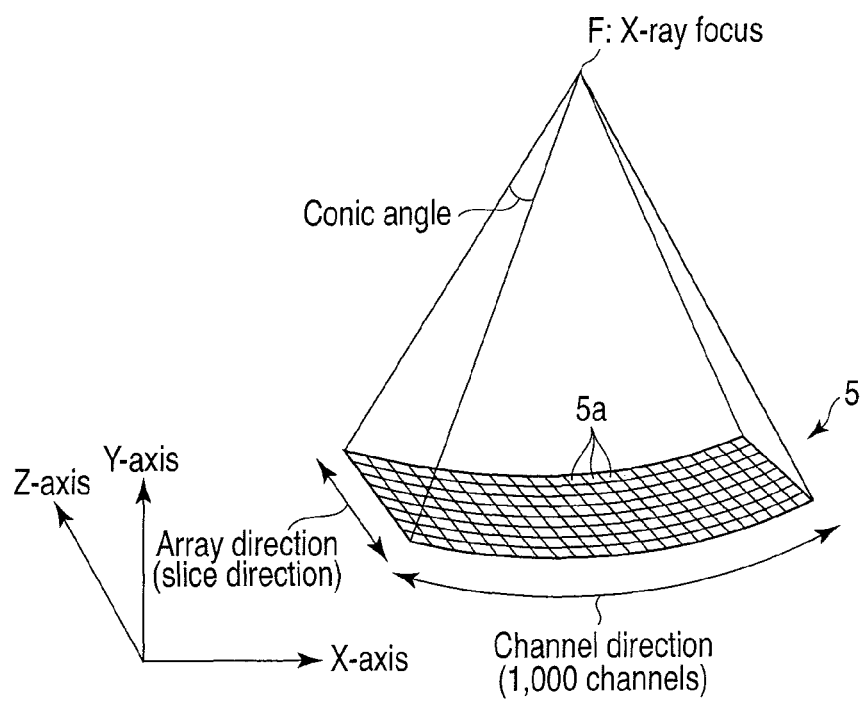
FIG. 3 is a view for explaining the two-dimensional array X-ray detector of the X-ray computed tomography apparatus.

FIG. 1 is a block diagram showing the arrangement of an X-ray computed tomography apparatus according to the first embodiment. FIG. 2 is a perspective view of the gantry in FIG. 1. FIG. 3 is a perspective view of the two-dimensional array detector in FIG. 1.

A gantry 1 as a projection data measurement system accommodates an X-ray source 3 which produces an X-ray beam having a pyramidal shape spreading in the array direction so as to irradiate a plurality of detector arrays with the X-rays and a two-dimensional array X-ray detector 5 having a plurality of detection elements 5a arrayed two-dimensionally.

The X-ray source 3 and the two-dimensional array X-ray detector 5 are mounted on a rotating ring 2 while facing each other through an object placed on a slide top of a bed 6.

The two-dimensional array X-ray detector 5 is mounted on the rotating ring 2 while a plurality of arrays of one-dimensional array detectors, each having a plurality of detection elements 5a arrayed one-dimensionally, are stacked on each other. In this case, one detection element 5a is defined as an element corresponding to one channel. X-rays from the X-ray source 3 are applied to an object through an X-ray filter 4. The two-dimensional array X-ray detector 5 detects the X-rays passing through the object as an electrical signal.

An X-ray controller 8 supplies a trigger signal to a high-voltage generator 7. The high-voltage generator 7 applies a high voltage to the X-ray source 3 at the timing of reception of the trigger signal. This makes the X-ray source 3 emit X-rays.

A gantry bed controller 9 controls the rotation of the rotating ring 2 of the gantry 1 and the sliding of the slide top of the bed 6. A system controller 10 as a control center for the overall system controls the X-ray controller 8 and the gantry bed controller 9 to repeat circular orbit scanning and the movement of the bed 6 in the body-axial direction. That is, the system controller 10 performs wide-range scanning operation by repeatedly circular orbit scanning operation in which the rotating ring 2 rotates at a predetermined angular velocity and the X-ray source 3 intermittently emits X-rays and moving the slide top in the body-axial direction at a predetermined velocity.

A data acquisition unit 11 amplifies an output signal from the two-dimensional array X-ray detector 5 and converts the signal into a digital signal for each channel. A reconstruction processing unit 12 receives the projection data output from the data acquisition unit 11.

The reconstruction processing unit 12 includes a storage unit 12a, a back-projection processing unit (back-projection unit) 13, an interpolation processing unit (interpolation unit) 14, a determination processing unit 15, and a setting unit 16. The reconstruction processing unit 12 performs reconstruction processing by a conic beam reconstruction method (Feldkamp (FDK) reconstruction method) which produces a CT image by performing back-projection processing in consideration of the conic angle of an X-ray beam, including the back-projection processing of obtaining back-projection data reflecting an X-ray absorbance for each voxel V based on projection data and the interpolation processing of interpolating the back-projection data. The reconstruction processing unit 12 functions as a medical image processing apparatus.

The back-projection processing unit 13 obtains back-projection data relating to each of a plurality of pixels defined in an imaging area by performing back projection of the acquired data. The interpolation processing unit 14 interpolates the data. The determination processing unit 15 determines whether an acquired image interval dZ is equal to a detector acquisition array width SW. The setting unit 16 sets the central positions of a plurality of pixels in an imaging area in reconstruction processing based on the determination result.

Figure 4:
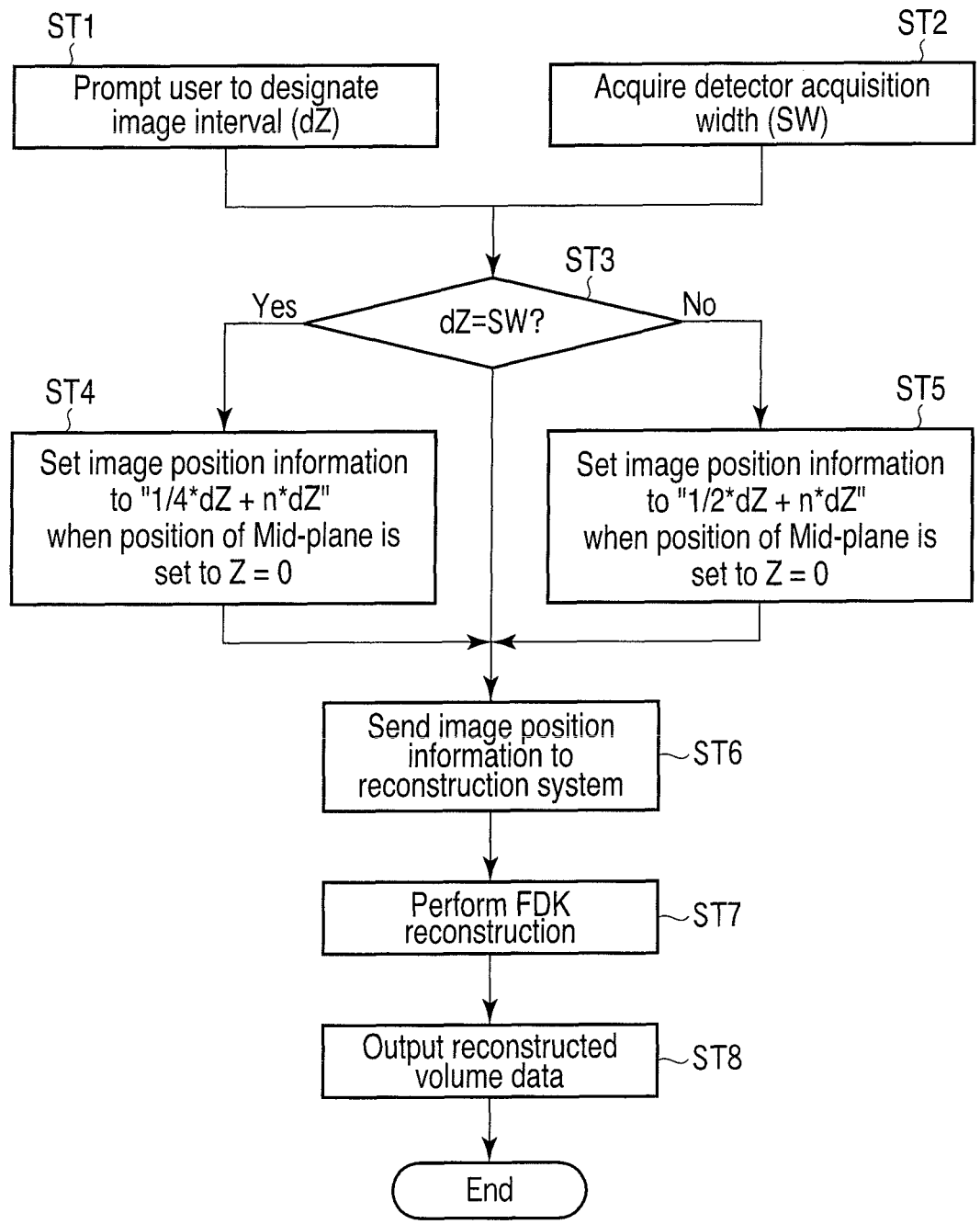
FIG. 4 is a flowchart showing a procedure for reconstruction processing according to the first embodiment.
Figure 5:
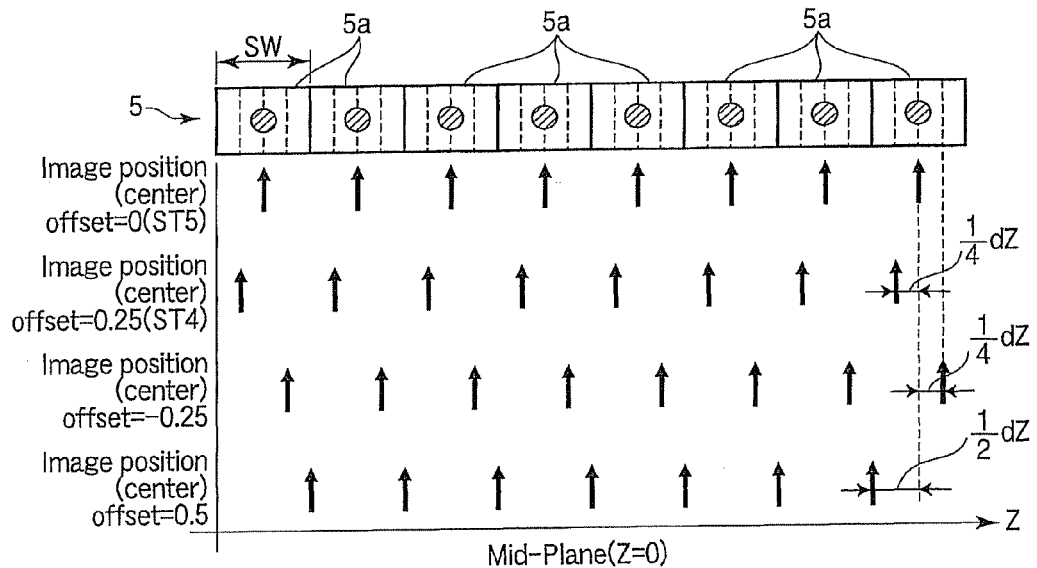
FIG. 5 is a view showing the positional relationship between image positions and detection elements in the reconstruction processing.
Figure 6:
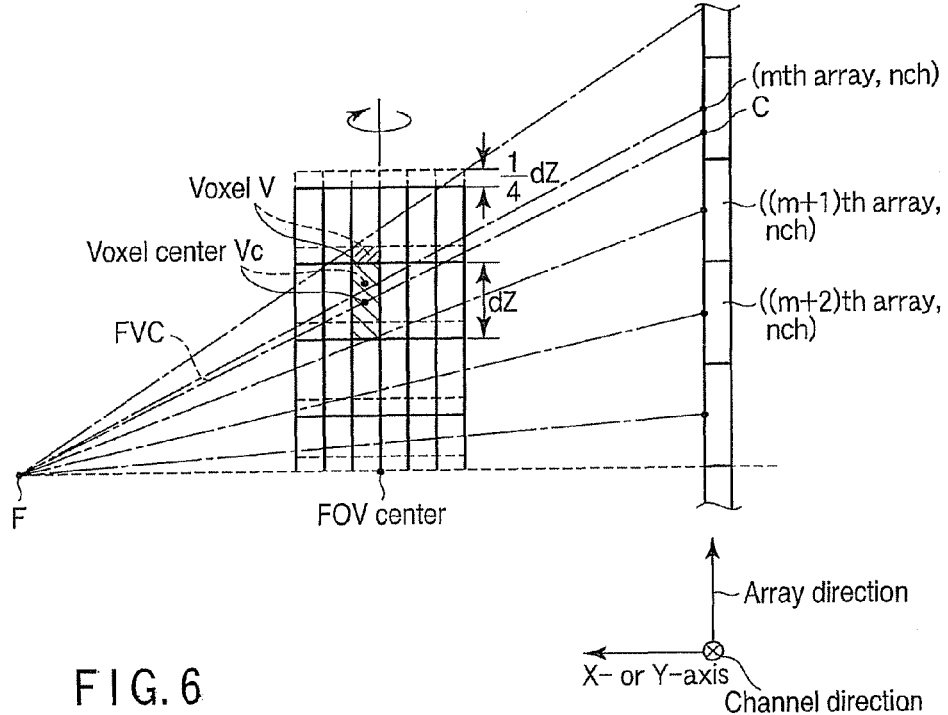
FIG. 6 is a view showing the relationship between X-ray beams and reconstruction voxels in the reconstruction processing.
Figure 7:
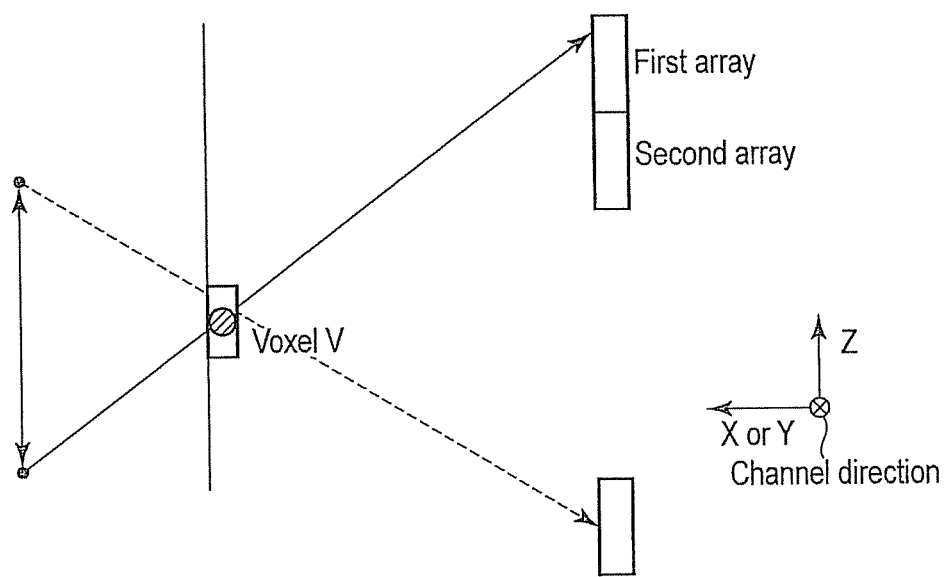
FIG. 7 is a view showing the relationship between an X-ray beam and a reconstruction voxel in the reconstruction processing when viewed from a direction perpendicular to the Z-axis.

An image reconstruction method according to this embodiment will be described with reference to FIGS. 4 to 8. FIG. 4 is a flowchart showing a procedure for reconstruction processing in this embodiment. FIG. 5 is a view showing the positional relationship between image positions and detection elements in reconstruction processing. FIG. 6 is a view for explaining calculated X-ray paths. FIGS. 7 and 8 are views for explaining extrapolation processing.

As shown in the flowchart of FIG. 4, first of all, in step ST1, the information of the image interval (pixel pitch) dZ is acquired. In this case, the image interval dZ is equal to a basic slice width SW, and is designated by, for example, input operation via an input device 17 by the user.

In step ST2, the information of the detector acquisition array width (detection element pitch) SW is acquired. In this case, this information is, for example, 0.5 mm.

In step ST3, this apparatus performs the determination processing of determining whether the image interval dZ and the detector acquisition array width SW, which are respectively acquired in steps ST1 and ST2 described above, are equal to each other.

If it is determined in step ST3 described above that the image interval dZ is equal to the detector acquisition array width SW (YES in step ST3), the setting unit 16 sets, in step ST4, image position to ¼*dZ+n*dZ when the position of the mid-plane (central cross-section in the array direction of the detector) is defined by Z=0. n is an integer.

As indicated by the broken line in FIG. 6, the position of a center Vc of each voxel V in the imaging area defined by the back-projection data is defined based upon a position which is located on a line segment passing through a center C of a corresponding X-ray detector element 5a and an X-ray focus F in the slice direction and is offset from the position where the line segment intersects an axis of rotation Z by ¼ the image interval dZ (¼ the basic slice thickness) in the slice direction.

If it is determined in step ST3 described above that the image interval dZ is different from the detector acquisition array width SW (NO in step ST3), the setting unit 16 sets, in step ST5, image position to ½*dZ+n*dZ when the position of the mid-plane is defined by Z=0, as shown in FIG. 5. That is, as indicated by the solid line in FIG. 6, the position of the center Vc (center of each pixel) of each voxel V is set based on a position which is located on a line segment passing through the center C of a corresponding X-ray detector element 5a and the X-ray focus F, and at the position where the line segment intersects the axis of rotation Z.

FIG. 5 shows the positional relationship between image positions and detection elements in a case in which image position is set to ½*dZ+n*dZ in step ST5 (which corresponds to a case in which offset=0 in Equation 6 to be described later) and a case in which image position information is set to ¼*dZ+n*dZ in step ST4 (which corresponds to a case in which offset=0.25 in Equation 6). FIG. 5 shows the positional relationship between image positions and detection elements in a case in which offset=−0.25 in Equation 6 and image position is set to ¾*dZ+n*dZ and a case in which offset=0.5 in Equation 6 and image position is set to n*dZ.

In step ST6, the defined positional information of the voxel V, i.e., the image position, is sent to the reconstruction processing unit 12.

In step ST7, this method performs reconstruction processing by the conic beam reconstruction method (Feldkamp (FDK) reconstruction method) of producing a CT image by performing back-projection processing in consideration of the conic angle of an X-ray beam. The FDK reconstruction method multiplies the weighted projection data of projection data by a value dependent on a Z-coordinate, and then performs convolution computation between this data and the same reconstruction function as the fan beam data (convolution computation). This method further performs the back-projection processing of performing back projection of the data obtained by the convolution computation onto a position offset from the path through which the X-ray beam has passed (from the focus to a channel of the detector) by ¼ the image interval dZ (basic slice thickness).

A specific example of back-projection processing will be described with reference to FIGS. 6 to 8 and 14. FIG. 6 is a schematic view showing the relationship between X-ray beams and reconstruction voxels in a given view I (rotational angle of the X-ray source 3 when the vertex position is set to, for example, 0°. FIG. 7 is a view showing the relationship between an X-ray beam and a reconstruction voxel in a given phase (given view I) when viewed from a direction perpendicular to the Z-axis. FIG. 8 is a view showing this relationship when viewed from a direction perpendicular to the X direction.

Note that in a scanning system using X-rays in a pyramidal shape like that in this embodiment, the imaging area (effective field of view) is formed into a cylindrical shape having a radius co centered on an axis of center of rotation, and the reconstruction processing unit 12 defines a plurality of voxels V (stereoscopic pixels or pixels) in this imaging area and obtains back-projection data for each voxel V. Note that the central positions Vc of the plurality of voxels V defined in this case are set as image positions, and the position information of each voxel V is set as image position information.

Consider back projection of the projection data of a view corresponding to the voxel V indicated by the hatching. Let C be a point where an extension of a straight line connecting the X-ray focus F and the center of the voxel V intersects the detector surface.

The point C exists on the nth and (n+1)th channels in the channel direction, and on the first array in the Z-axial direction. The point C is located on the upper side of the central Z-coordinate of the uppermost detector array.

According to Equation 1, back-projection data Back (I) is obtained by extrapolating four data of the nth and (n+1)th channels of the first and second arrays using the inverse ratios of the distances.

$$\text{Back}(I) = -\frac{Z(1)}{Z(2)-Z(1)}\left[\frac{L(n+1)}{L(n+1)+L(n)}D(n,2) + \frac{L(n)}{L(n+1)+L(n)}D(n+1,2)\right] + \frac{Z(2)}{Z(2)-Z(1)}$$

(Equation 1)

$$\left[\frac{L(n+1)}{L(n+1)+L(n)}D(n,1)+\frac{L(n)}{L(n+1)+L(n)}D(n+1)\right]$$

where Z(1) and Z(2) are the distances from the channel centers of the mth and (m+1)th arrays to the point C in the Z-direction, and L(n) and L(n+1) are the distances from the centers of the nth and (n+1)th channels to the point C on an X-Y plane.

When the intersection is located below the channel center of the lowermost array of the detector, it is possible to perform extrapolation in the same manner as described above and perform substitutions of Z(1)→Z(N) and Z(2)→Z(N−1) in Equation 1.

This apparatus performs back-projection processing through 360° and produces reconstructed volume data from these back-projection data. In step ST8, the three-dimensional image data or tomographic data having undergone reconstruction processing is sent to a display device 18 and displayed as a three-dimensional image or tomogram.

In the back-projection processing described above, a specific Z-position at which data is to be used for back projection is calculated by Equation 2. When back projection is to be performed for a voxel at a position spaced apart from the mid-plane by z and from the rotation center by r as shown in FIG. 14, a Z-position $Z_D$ of a point where an extension of a line connecting the X-ray source and the voxel intersects the detector can be calculated by Equation 2.

$$Z_D(r,z) = \frac{FCD}{FCD-r} \cdot z \quad \text{(Equation 2)}$$

Based on the result obtained by Equation 2, this apparatus then calculates "how much $Z_D$ is spaced apart from neighboring pixel?" using Equation 3. The nearer this value to 0 or 1, the weaker the influence of interpolation in the Z-direction. The nearer the value to 0.5, the stronger the influence of interpolation. Let SW be a detector acquisition slice width (=detector element pitch witch).

$$\hat{Z}_D(r,z) = \text{MOD}\left(\frac{Z_D(r,z)+0.5 \cdot SW}{SW},1\right) \quad \text{(Equation 3)}$$

if, $\hat{Z}_D(r,z) > 0.5$, $\hat{Z}_D(r,z) = 1 - \hat{Z}_D(r,z)$

This apparatus then performs calculation using Equations 4 in consideration of the influence of cancellation with back projection from the 180° opposite side.

$$\hat{Z}_D^+(r,z) = \hat{Z}_D(r,z) \quad \text{(Equation 4)}$$
$$\hat{Z}_D^-(r,z) = \hat{Z}_D(-r,z)$$

Note that since the X-ray dose is proportional to the inverse ratio of the square of image noise, a noise figure Noise(r, z) which the voxel has is expediently defined like Equation 5.

Figure 9:
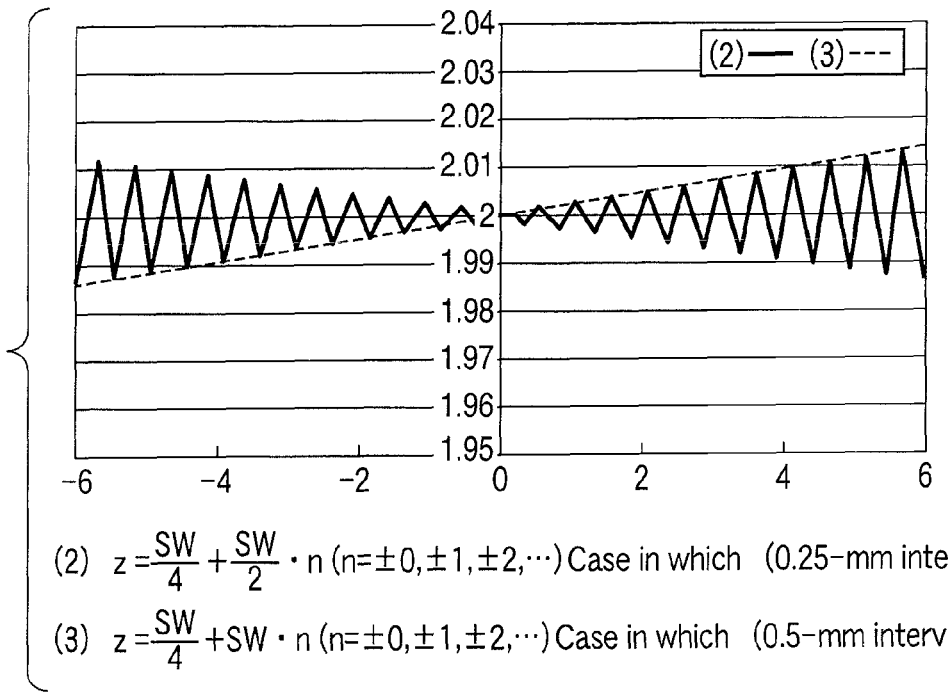
FIG. 9 is a graph showing the noise of reconstructed volume data obtained by reconstruction processing according to the first embodiment.

FIG. 9 is a graph showing the noise using Equation 5. The abscissa represents z; and the ordinate, the noise. In this case, FCD=600 and SW=0.5.

$$\text{Noise}(r,z) = \frac{1}{\sqrt{\frac{\hat{Z}_D^+(r,z)+\hat{Z}_D^-(r,z)}{2}}} \quad \text{(Equation 5)}$$

FIG. 9 shows noise in a case (2) in which the interval dZ is set to 0.25 mm when SW=0.5, and noise in a case (3) in which the interval dZ is set to 0.5 mm when SW=0.5, and the central position of each pixel is offset by ¼ dZ. In these cases, the noise falls within about 2.

Figure 11:
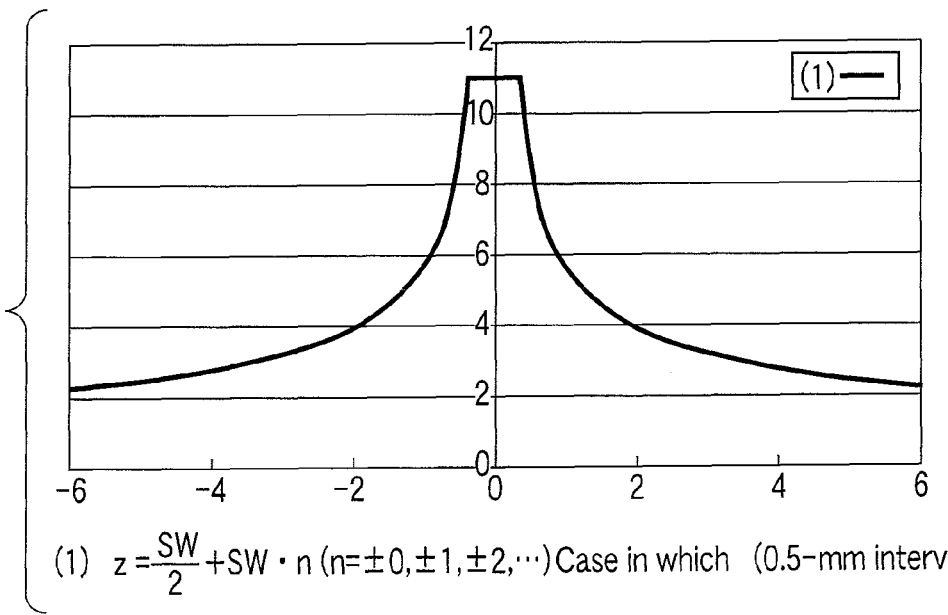
FIG. 11 is a graph showing noise in an example of reconstructed volume data.

FIG. 11 shows, as a comparative example (1), noise in a case in which the interval is set to 0.5 mm when SW=0.5, and the central position of each pixel is set to a position corresponding to the center of a corresponding X-ray detection element. In this case, the noise increases up to about 11. As shown in FIG. 11, the noise rapidly increases as z approaches zero when the interval is 0.5 mm when SW=0.5. This is because, as defined by Equation 3, as z approaches zero, the influence of interpolation in the Z-direction quickly decreases.

As shown in FIG. 9, the reconstructed image in this embodiment is free from such influence. Obviously, when the interval is 0.5 mm, it is possible to prevent noise by offsetting the central position of each pixel from a position corresponding to the center by ¼ the image interval.

FIG. 10 shows an image obtained by expressing the reconstructed volume data obtained by the above operation in MIP. Since this MIP image is interpolated uniformly as a whole, no artifact appears at the central position.

FIG. 12 shows, as a comparative example, an MIP image of the reconstructed volume data obtained by back projection onto a path through which X-rays have passed (from the focus to a channel of the detector). In this reconstruction, since almost no interpolation is performed for back-projection data corresponding to the detection element at the central position in the slice direction, an image SD near the axis of rotation as the central position and the mid-plane deteriorates. When this image is expressed in MIP, as shown in FIG. 12, a cross-shaped artifact is formed at the central position corresponding to a position near the axis of rotation and the mid-plane. Note that this artifact appears circular when viewed from the slice direction (Z-direction), and appears cross-shaped as shown in FIG. 12 when viewed from the directions indicated by arrows X and Y.

According to this embodiment, the following effects can be obtained. That is, it is possible to reduce the unevenness of the degree of interpolation due to the differences in position between a plurality of juxtaposed detection elements by offsetting the position of each voxel V in the imaging area subjected to back projection from a corresponding X-ray path by ¼ the image interval (slice thickness). This makes it possible to eliminate or reduce artifacts appearing in an MIP image. This also allows to obtain the effect of maximizing the artifact reduction effect by setting the offsetting distance to ¼ the slice thickness.

Another embodiment will consider changes in noise with changes in offset from the center of a corresponding X-ray detection element. Consider, in this case, Equation 6 given below as an equation for setting the central positions of a plurality of pixels in an imaging area in reconstruction processing.

$$z = SW/2 - SW \cdot \text{Offset} + SW \cdot n \, (n=\pm 0, \pm 1, \pm 2, \ldots, \text{Offset}=[0, 0.25, 0.5]) \quad \text{(Equation 6)}$$

where SW·offset is the offset. Since an image interval dZ is equal to a detector acquisition array width SW, SW is replaced with dZ. Note that offsets were set within the range of 0 to 0.5 in consideration of symmetry.

FIG. 5 shows the positional relationship between image positions and detection elements when the offset in Equation 6 is set to 0, 0.25, −0.25, and 0.5.

Assume that the central positions of a plurality of pixels in the imaging area in reconstruction processing each are set to SW/2 which is a position corresponding to the center of a corresponding X-ray detection element (are not offset). In this case, the offset is zero, which is equivalent to the case (1) in FIG. 11. In contrast, when each image position is offset from the center of a corresponding X-ray detection element by dZ/4, the offset is 0.25, which is equivalent to the case (3) in FIG. 9. When the central positions of a plurality of pixels are offset from the center of the corresponding X-ray detection element by dZ/2, the offset is 0.5. Although the offset direction can be either the positive or negative direction, the following will exemplify a case in which the offset direction is the negative direction.

FIG. 13 is a graph obtained by calculating the maximum and minimum values of Noise ( ) calculated by Equation 6, in an interval [−10, 10], with both the image interval dZ and the detector acquisition array width SW being set to 0.5 mm, and calculating the ratios of the maximum and minimum values. FIG. 13 shows the relationship between the offsets and noise differences of reconstructed volume data obtained by reconstruction processing. The smaller this value, the smaller the noise difference in the Z-direction, and the smaller the artifact. It is obvious from FIG. 13 that when offset=0, the noise difference is largest, and when offset=0.25, the noise difference is smallest, and that the noise difference when offset=0.5 is larger than that when offset=0.25 but is smaller than that when offset=0.

It is therefore ideal to offset each image position from a corresponding normal image position by ¼ the image interval dZ. However, it is possible to obtain the same effect even by offsetting each image position by a value between ¼ the image interval dZ and ½ the image interval dZ.

In practicing the present invention, it is obvious that the constituent elements of the present invention, such as specific shapes including the forms of various members, can be variously changed and implemented without departing from the spirit and scope of the invention. Although an X-ray conic beam in a pyramidal shape has been exemplified, the present invention can be applied to X-rays in a conical shape.

In addition, the algorithm and interpolation method to be used for reconstruction processing are not limited those described above.

The above embodiment has exemplified, as an especially effective example, the case in which the offset is set to ¼ the image interval dZ when SW=dZ. However, the present invention is not limited to this. For example, it is possible to change the offset in accordance with various conditions. That is, the set value of image position in step ST4 in FIG. 4 can be changed in accordance with various conditions. In this case as well, it is possible to reduce the unevenness of the degree of interpolation due to the differences in position between a plurality of juxtaposed detection elements by setting the central positions of a plurality of pixels in an imaging area in reconstruction processing to positions offset from the positions corresponding to the centers of X-ray detection elements in the slice direction. This makes it possible to eliminate or reduce artifacts appearing in an MIP image.

It is obvious that the above embodiments can be variously modified and executed without departing from the spirit and scope of the present invention.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An X-ray computed tomography apparatus comprising:
   an X-ray source which irradiates an object with X-rays spreading in a slice direction;
   an X-ray detector comprising a plurality of X-ray detection elements which are juxtaposed in the slice direction and detect X-rays transmitted through the object;
   a reconstruction unit which comprises a back-projection unit which obtains back-projection data relating to each of a plurality of pixels having a predetermined pitch and being defined in an imaging area by performing back projection of data acquired by the X-ray detector, and an interpolation unit which interpolates the acquired data, and performs reconstruction processing for an image; and
   a setting unit which sets central positions of the imaging area in the reconstruction processing to positions offset from positions corresponding to centers of the plurality of X-ray detection elements in the slice direction.

2. The apparatus according to claim 1, wherein
   if a pitch of the plurality of X-ray detection elements in the slice direction is equal to the pitch of the plurality of pixels in the slice direction, central positions of the plurality of pixels in the imaging area are offset from the positions corresponding to the centers of the plurality of X-ray detection elements in the slice direction, and
   if the pitch of the plurality of X-ray detection elements in the slice direction is different from the pitch of the plurality of pixels in the slice direction, the central positions of the plurality of pixels in the imaging area are set to the positions corresponding to the centers of the plurality of X-ray detection elements.

3. The apparatus according to claim 1, wherein a position of a center of the X-ray detection element is defined based on a position where a line segment connecting the center of the X-ray detection element and a focus of X-rays intersects an axis of rotation of the X-ray source and the X-ray detector.

4. The apparatus according to claim 1, wherein
   the X-ray source moves along a circular orbit relative to the object, and
   the X-ray detector comprises a two-dimensional array X-ray detector comprising a plurality of X-ray detection elements arrayed two-dimensionally.

5. The apparatus according to claim 1, wherein the central positions of the plurality of pixels in the imaging area are set to positions offset from the positions corresponding to the centers of the plurality of X-ray detection elements in the slice direction by ¼ the pitch of the plurality of pixels in the slice direction.

6. A medical image processing apparatus comprising:
   a storage unit which stores data acquired by an X-ray CT apparatus;
   a reconstruction unit which comprises a back-projection unit which obtains back-projection data relating to each of a plurality of pixels having a predetermined pitch and being defined in an imaging area by performing back projection of the acquired data, and an interpolation unit which interpolates the acquired data from the storage unit, and performs reconstruction processing for an image; and a setting unit which sets central positions of the imaging area in the reconstruction processing to positions offset from positions corresponding to centers of a plurality of X-ray detection elements of the x-ray CT apparatus in a slice direction.

7. The apparatus according to claim 6, wherein if a pitch of the plurality of X-ray detection elements in the slice direction is equal to the pitch of the plurality of pixels in the slice direction, central positions of the plurality of pixels in the imaging area are offset from the positions corresponding to the centers of the plurality of X-ray detection elements in the slice direction, and if the pitch of the plurality of the X-ray detection elements in the slice direction is different from the pitch of the plurality of pixels in the slice direction, the central positions of the plurality of pixels in the imaging area are set to the positions corresponding to the centers of the plurality of X-ray detection elements.

8. The apparatus according to claim 6, wherein a position of a center of the X-ray detection element is defined based on a position where a line segment connecting the center of the X-ray detection element and a focus of X-rays intersects an axis of rotation of an X-ray source and the X-ray detection element.

9. The apparatus according to claim 6, further comprising:

an X-ray source of the X-ray CT apparatus moves along a circular orbit relative to an object, and irradiates the object with X-rays spreading in the slice direction, and an X-ray detector of the X-ray CT apparatus comprises a two-dimensional array X-ray detector comprising a plurality of X-ray detection elements arrayed two-dimensionally.

10. The apparatus according to claim 6, wherein the central positions of the plurality of pixels in the imaging area are set to positions offset from the positions corresponding to the centers of the plurality of X-ray detection elements in the slice direction by ¼ the pitch of the plurality of pixels in the slice direction.

11. An X-ray computed tomography method using an X-ray computed tomography apparatus, the method comprising:

irradiating an object with X-rays spreading in a slice direction;

detecting X-rays transmitted through the object by using an X-ray detector comprising a plurality of x-ray detection elements which are juxtaposed in the slice direction;

performing reconstruction processing for an image comprising obtaining back-projection data relating to each of a plurality of pixels defined in an imaging area by performing back-projection of the data acquired in detecting and interpolating the acquired data; and setting central positions of the imaging area in the reconstruction processing to positions offset from positions corresponding to centers of the plurality of x-ray detection elements in the slice direction.

12. The X-ray computed tomography method according to claim 11, wherein the central positions of the plurality of pixels in the imaging area are set to positions offset from the positions corresponding to the centers of the plurality of X-ray detection elements in the slice direction by ¼ the pitch of the plurality of pixels in the slice direction.

13. A medical image processing method using a medical image processing apparatus, the method comprising:

storing data acquired by an x-ray CT apparatus;

performing reconstruction processing for an image comprising obtaining back-projection data relating to each of a plurality of pixels defined in an imaging area by performing back-projection of the acquired data and interpolating the acquired data; and setting central positions of the imaging area in the reconstruction processing to positions offset from positions corresponding to centers of a plurality of x-ray detection elements in a slice direction.

14. The medical image processing method according to claim 13, wherein the central positions of the plurality of pixels in the imaging area are set to positions offset from the positions corresponding to the centers of the plurality of X-ray detection elements in the slice direction by ¼ the pitch of the plurality of pixels in the slice direction.

* * * * *